United States Patent
Andrés-Gil et al.

(10) Patent No.: US 11,045,562 B2
(45) Date of Patent: *Jun. 29, 2021

(54) RADIOLABELLED MGLUR2/3 PET LIGANDS

(71) Applicant: Janssen Pharmaceutica NV, Beerse (BE)

(72) Inventors: José Ignacio Andrés-Gil, Madrid (ES); Michiel Luc Maria Van Gool, Madrid (ES); Guy Maurits R Bormans, Rotselaar (BE); Joost Verbeek, Enkhuizen (NL)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/061,674

(22) PCT Filed: Dec. 16, 2016

(86) PCT No.: PCT/EP2016/081537

§ 371 (c)(1),
(2) Date: Jun. 13, 2018

(87) PCT Pub. No.: WO2017/103179

PCT Pub. Date: Jun. 22, 2017

(65) Prior Publication Data

US 2018/0369429 A1 Dec. 27, 2018

(30) Foreign Application Priority Data

Dec. 18, 2015 (EP) .................................... 15201239

(51) Int. Cl.
| | |
|---|---|
| *A61K 49/04* | (2006.01) |
| *A61K 51/04* | (2006.01) |
| *C07B 59/00* | (2006.01) |
| *C07D 487/04* | (2006.01) |
| *C07D 241/50* | (2006.01) |
| *C07D 253/08* | (2006.01) |

(52) U.S. Cl.
CPC ........ *A61K 51/0459* (2013.01); *C07B 59/002* (2013.01); *C07D 241/50* (2013.01); *C07D 253/08* (2013.01); *C07D 487/04* (2013.01)

(58) Field of Classification Search
CPC .............. A61K 51/0459; C07B 59/002; C07D 487/04; C07D 241/50; C07D 253/08
USPC ....................................................... 424/9.44
See application file for complete search history.

(56) References Cited

U.S. PATENT DOCUMENTS

| | | | |
|---|---|---|---|
| 10,005,785 B2 * | 6/2018 | Alonso-de Diego | ........................ C07D 487/04 |
| 2001/0011087 A1 | 8/2001 | Wehner et al. | |
| 2003/0027807 A1 | 2/2003 | Wehner et al. | |
| 2005/0107412 A1 | 5/2005 | Maw et al. | |
| 2013/0310555 A1 | 11/2013 | Chong | |
| 2015/0005313 A1 | 1/2015 | Brodney et al. | |

FOREIGN PATENT DOCUMENTS

| | | |
|---|---|---|
| EP | 0756200 B1 | 1/1997 |
| EP | 2327704 A1 | 6/2011 |
| EP | 2666775 A1 | 11/2013 |
| JP | 2007507446 A | 3/2007 |
| JP | 2008503510 A | 2/2008 |
| JP | 2008530042 A | 8/2008 |
| JP | 2008534455 | 8/2008 |
| JP | 2012501352 | 1/2012 |
| JP | 2013189395 A | 9/2013 |
| JP | 2016124810 | 7/2016 |
| WO | 2002/096873 A1 | 12/2002 |
| WO | 2005/002552 A2 | 1/2005 |
| WO | 2005/040171 A1 | 5/2005 |
| WO | 2005/061507 A1 | 7/2005 |
| WO | 2005/123738 A1 | 12/2005 |
| WO | 2006/030847 A1 | 3/2006 |
| WO | 2006/050803 A1 | 5/2006 |
| WO | 2006/084634 A1 | 8/2006 |
| WO | 2006/099972 | 9/2006 |
| WO | 2007/084314 A2 | 7/2007 |
| WO | 2007092416 A2 | 8/2007 |
| WO | 2008/001115 A2 | 1/2008 |
| WO | 2008/141239 A1 | 11/2008 |
| WO | 2009/095872 A2 | 8/2009 |
| WO | 2009/118292 A1 | 10/2009 |
| WO | 2009/130232 A1 | 10/2009 |
| WO | 2010/025890 | 3/2010 |

(Continued)

OTHER PUBLICATIONS

Cai et al. Eur. J. Org. Chem. 2008, 2853-2873.*
Alfonso R. Gennaro, Pharmaceutical Sciences, Remington's, 1990, pp. 1435-1712, 18th edition.
Alper, et al., Agonist-Stimulated [35S]GTBgS Binding, Current Protocols in Pharmacology, 1998, pp. 1-10, vol. 2 Issue 6.
Andres, et al., Synthesis, Evaluation, and Radiolabeling of New Potent Positive Allosteric Modulators of the Metabotropic Glutamate Receptor 2 as Potential Tracers for Positron Emission Tomography Imaging, Journal of Medicinal Chemistry, Sep. 20, 2012, pp. 8685-8699, vol. 55.

(Continued)

*Primary Examiner* — Michael G. Hartley
*Assistant Examiner* — Sean R Donohue
(74) *Attorney, Agent, or Firm* — Fay Kaplun & Marcin, LLP (57) ABSTRACT

The present invention relates to novel, radiolabeled mGluR2/3 ligands, selective versus other mGlu receptors which are useful for imaging and quantifying the metabotropic glutamate receptor mGlu2 and 3 in tissues, using positron-emission tomography (PET). The invention is also directed to compositions comprising such compounds, to processes for preparing such compounds and compositions, to the use of such compounds and compositions for imaging a tissue, cells or a mammal, in vitro or in vivo and to precursors of said compounds.

4 Claims, 5 Drawing Sheets

(56) References Cited

FOREIGN PATENT DOCUMENTS

| WO | 2010/130423 A1 | 11/2010 | | |
|---|---|---|---|---|
| WO | 2010/130424 | 11/2010 | | |
| WO | 2012/035078 A1 | 3/2012 | | |
| WO | 2012/062752 A1 | 5/2012 | | |
| WO | 2012/083224 A1 | 6/2012 | | |
| WO | 2012/143726 A1 | 10/2012 | | |
| WO | 2013/012915 A1 | 1/2013 | | |
| WO | 2013/012918 A1 | 1/2013 | | |
| WO | 2013/066736 A1 | 5/2013 | | |
| WO | 2013/154878 A1 | 10/2013 | | |
| WO | 2013/156869 A1 | 10/2013 | | |
| WO | 2013/174822 A1 | 11/2013 | | |
| WO | 2013/192343 A1 | 12/2013 | | |
| WO | 2013/192347 A1 | 12/2013 | | |
| WO | 2013/192350 A1 | 12/2013 | | |
| WO | 2014/008197 A1 | 1/2014 | | |
| WO | 2014/064028 A1 | 5/2014 | | |
| WO | 2014/195311 A1 | 12/2014 | | |
| WO | 2014/207082 A1 | 12/2014 | | |
| WO | WO-2014195311 A1 * | 12/2014 | ........... | C07D 487/04 |
| WO | 2016/016381 A1 | 2/2016 | | |
| WO | 2016/016382 A1 | 2/2016 | | |
| WO | 2016/016383 A1 | 2/2016 | | |
| WO | 2016/016395 A1 | 2/2016 | | |
| WO | 016380 | 2/2016 | | |
| WO | WO-2016016395 A1 * | 2/2016 | ........... | C07D 487/04 |
| WO | 2016/087487 A1 | 6/2016 | | |
| WO | 2016/087489 A1 | 6/2016 | | |
| WO | 2017/103179 A1 | 6/2017 | | |
| WO | 2017/103182 A1 | 6/2017 | | |

OTHER PUBLICATIONS

Bigotti, et al, Synthesis of C[CH(RF)NH]Gly-peptides: The dramatic effect of a single fluorine atom on the diastereocontrol of the key aza-Michael reaction, Journal of Fluorine Chemistry, Jun. 27, 2008, pp. 767-774, 129.

Cid, et al., Discovery of 1,4-Disubstituted 3-Cyano-2-pyridones: A New Class of Positive Allosteric Modulators of the Metabotropic Glutamate 2 Receptor, Journal of Medicinal Chemistry, Feb. 24, 2012, pp. 2388-2405, vol. 55, American Chemical Society.

D. S. Ermolat'Ev et al, One-pot microwave-assisted protocol for the synthesis, Mol Divers, Aug. 26, 2010, pp. 491-496, vol. 15.

Dinklo Theo et al, Characterization of 2-[[4-Fluoro-3-(trifluoromethyl)phenyl]amino]-4-(4-pyridinyl)-5-thiazolemethanol (JNJ-1930942), a Novel Positive Allosteric Modulator of the 7 Nicotinic Acetylcholine Receptor☐S, The Journal of Pharmacology and Experimental Therapeutics, 2011, pp. 560-574, vol. 336 No. 2.

Embrechts S. et al, Longitudinal characterisation of the TauPS2APP mouse model of Alzheimer's disease in a two trial discrimination task of visuo-spatial recognition memory, 45th European Brain and Behaviour Society Meeting Sep. 6-9, 2013 Munich, Sep. 6, 2009, p. 202, not applicable.

Farinha, et al., Research Paper Molecular determinants of positive allosteric modulation of the human metabotropic glutamate receptor 2, British Journal of Pharmacology, 2015, pp. 2383-2396, vol. 172.

Ferraguti, et al, Metabotropic glutamate receptors, Cell & Tissue Research, Jul. 18, 2006, pp. 483-504, vol. 326.

Gilfillian, et al, Synthesis and biological evaluation of novel 2,3-dihydro-1H-1,5-benzodiazepin-2-ones; potential imaging agents of the metabotropic glutamate 2 receptor, Med. Chem. Commun., May 29, 2013, pp. 1118-1123, vol. 4 Issue 7.

Goeldner, et al., Cognitive impairment in major depression and the mGlu2 receptor as a therapeutic target, Neuropharmacology, Aug. 3, 2013, pp. 337-346, vol. 64

Guy A. Higgins et al., Pharmacological manipulation of mGlu2 receptors influences, Neuropharmacology, 2004, pp. 907-917, vol. 46.

Hackam, et al, "Translation of Research Evidence From animals to Humans", JAMA, vol. 296 (14): pp. 1731-1732 (2006).

Hickinbottom, English translation of the relevent from reaction of organic complonents, Reactions of organic compounds, 1939, pp. 360-362, Page Number.

Hoffmann-La Roche, ARTDeCo study: A Study RO4995819 in Patients with Major Depressive Disorder and Inadequate Response to Ongoing Antidepressant Treatmnet, ClinicialTrials.gov, Oct. 24, 2011, Placebo, NCT01457677.

Kelmendi, et al, The role of the Glutamatergic system in the pathophysiology and treatment of mood disorders, Primary Psychiatry, 2006, pp. 80-86, vol. 13 Issue 10.

Koike, et al., Role of BDNF/TrkB signaling in antidepressant-like effects of a group II metabotropic glutamate receptor antagonist in animal models of depression, Behavioural Brain Research, 2013, pp. 48-52, vol. 238.

Li Jingjie et al, Palladium-Catalyzed Oxidative Rearrangement of Tertiary Allylic Alcohols to Enones with Oxygen in Aqueous Solvent, Organic Letters, Oct. 3, 2014, pp. 5370-5373, No. 16.

Malkov, et al., On the Selective N-Methylation of BOC-Protected Amino Acids ., J. Org. Chem., Oct. 7, 2009, pp. 8425-8427, vol. 74 Issue 21.

Moscow., Chemical Encyclopedia, Soviet encyclopedia, 1988, pp. 242-243, vol. 1.

Niswender, et al., Metabotropic Glutamate Receptors: Physiology, Pharmacology, and Disease, Annu.Rev. Pharmacol.Toxicol., 2010, pp. 295-322, vol. 50.

Schaffhauser et al, Pharmacological Characterization and Identification of Amino Acids Involved in the Positive Modulation of Metabotropic Glutamate Receptor Subtype 2, Molecular Pharmacology, Jun. 13, 2003, pp. 798-810, vol. 64, No. 4.

Shigemoto, et al., Differential Presynaptic Localization of Metabotropic Glutamate Receptor Subtypes in the Rat Hippocampus, The Journal of Neuroscience, Oct. 1, 1997, pp. 7503-7522, vol. 17 Issue 19, Society for Neuroscience.

Suzuki, et al., Rapid Coupling of Methyl Iodide with Aryltributylstannanes Mediated by Palladium(0) Complexes: A General Protocal for the Synthesis of CH3-Labeled PET Tracers., Chem. Eur. J., 1997, pp. 2039-2042, vol. 3 Issue 12.

V. Craig Jordan, "Tamoxifen: A Most Unlikely Pioneering Medicine", Nature Reviews Drug Discovery, 2003, pp. 205-213, vol. 2.

Vippagunta et al, Crystalline solids, Advanced Drug Delivery Reviews, May 16, 2001, pp. 3-26, vol. 48 No. 1.

Bell et al., "DSM-IV: Diagnostic and Statistical Manual of Mental Disorders," JAMA, vol. 272, No. 10, Sep. 1994, pp. 828-829.

Higgins et al., "Pharmacological manipulation of mGlu2 receptors influences cognitive performance in rodents", Neuropharmacology, vol. 46, May 2004, pp. 907-917.

Hoffmann-La Roche, ClinicalTrials.gov Identifier NCT01457677, Feb. 2014, 3 sheets.

Int. search report for PCT/EP2014/061478—JAB6015, Aug. 2014, 4 sheets.

Int. search report for PCT/EP2015/067530—JAB6033, Nov. 2015, 3 sheets.

Int. search report for PCT/EP2015/067533—JAB6034, Oct. 2015, 3 sheets.

Int. search report for PCT/EP2015/067534—JAB6036, Sep. 2015, 3 sheets.

Int. search report for PCT/EP2015/067538—JAB6037, Sep. 2015, 4 sheets.

Int. search report for PCT/EP2015/067572—JAB6035, Sep. 2015, 4 sheets.

Int. search report for PCT/EP2015/078296—JAB6049, Feb. 2016, 5 sheets.

Int. search report for PCT/EP2015/079216—JAB6052, Feb. 2016, 5 sheets.

Int. search report for PCT/EP2015/078285—JAB6045, Feb. 2016, 4 sheets.

Int. search report for PCT/EP2015/078285—JAB6080, Mar. 2017, 5 sheets.

(56) References Cited

OTHER PUBLICATIONS

Sheffler et al., "Recent Progress in the Synthesis and Characterization of Group II Metabotropic Glutamate Receptor Allosteric Modulators", ACS Chemical Neuroscience, vol. 2, Apr. 2011, pp. 382-393.

* cited by examiner

RADIOLABELLED MGLUR2/3 PET LIGANDS

This application is a 371 National Stage Application of International Application No. PCT/EP2016/081537 with an international filing date of Dec. 16, 2016 and claims the benefit of priority to European Application No. EP15201239.9 filed Dec. 18, 2015, the entire disclosures of each of which are hereby incorporated in their entirety.

FIELD OF THE INVENTION

The present invention relates to novel, radiolabelled mGluR2/3 ligands, selective versus other mGlu receptors which are useful for imaging and quantifying the metabotropic glutamate receptor mGlu2 and 3 in tissues, using positron-emission tomography (PET). The invention is also directed to compositions comprising such compounds, to processes for preparing such compounds and compositions, to the use of such compounds and compositions for imaging a tissue, cells or a mammal, in vitro or in vivo and to precursors of said compounds.

BACKGROUND OF THE INVENTION

The glutamatergic system in the CNS is one of the neurotransmitter systems that play a key role in several brain functions. Metabotropic glutamate receptors (mGluR) belong to the G-protein-coupled family, and eight different subtypes have been identified to date, which are distributed to various brain regions (Ferraguti & Shigemoto, Cell & Tissue Research, 326:483-504, 2006). mGluRs participate in the modulation of synaptic transmission and neuronal excitability in the CNS by the binding of glutamate. This activates the receptor to engage intracellular signaling partners, leading to cellular events (Niswender & Conn, Annual Review of Pharmacology & Toxicology 50:295-322, 2010).

mGluRs are further divided into three subgroups based on their pharmacological and structural properties: group-I (mGluR1 and mGluR5), group-II (mGluR2 and mGluR3) and group-III (mGluR4, mGluR6, mGluR7 and mGluR8). Group-II ligands, both orthosteric and allosteric modulating, are considered to be potentially useful in the treatment of various neurological disorders, including psychosis, mood disorders, Alzheimer's disease and cognitive or memory deficiencies. This is consistent with their primary localisation in brain areas such as the cortex, hippocampus and the striatum (Ferraguti & Shigemoto, Cell & Tissue Research 326:483-504, 2006). Particularly antagonists and negative allosteric modulators are reported to hold potential for the treatment of mood disorders and cognitive or memory dysfunction. This is based on findings with group-II receptor antagonists and negative allosteric modulators tested in laboratory animals subjected to a range of experimental conditions deemed relevant to these clinical syndromes (Goeldner et al, Neuropharmacology 64:337-346, 2013). Clinical trials are, for example, underway with mGluR2/3 antagonist RO4995819 (F. Hoffmann-La Roche Ltd.) in adjunctive therapy in patients with Major Depressive Disorder having inadequate response to ongoing antidepressant treatment (ClinicalTrials.gov Identifier NCT01457677, retrieved 19 Feb. 2014). WO 2013066736 (Merck Sharp & Dohme Corp.) describes quinoline carboxamide and quinoline carbonitrile compounds as mGluR2 NAMs. WO2013174822 (Domain therapeutics) describes 4H-pyrazolo[1,5-a]quinazolin-5-ones and 4H-pyrrolo [1,2-a]quinazolin-5-ones and in vitro mGluR2 NAM activity thereof. WO 2014064028 (F. Hoffman-La Roche AG) discloses a selection of mGlu2/3 negative allosteric modulators and their potential use in the treatment of Autistic Spectrum Disorders (ASD). WO2014195311 (Janssen Pharmaceutica NV) discloses 6,7-dihydropyrazolo[1,5-a]pyrazine-4(5H)-one compounds and their use as mGluR2 NAMs.

The group-II receptors are mainly located on presynaptic nerve terminals where they exert a negative feedback loop to the release of glutamate into the synapse (Kelmendi et al, Primary Psychiatry 13:80-86, 2006). Functional inhibition of these receptors by antagonists or negative allosteric modulators therefore lifts the brake on glutamate release, resulting in enhanced glutamatergic signaling. This effect is believed to underlie the antidepressant-like and procognitive effects observed in preclinical species with inhibitors of the Group-II receptor. In addition, treatment of mice with group-II orthosteric antagonists has been shown to enhance signaling by growth factors such as brain derived neurotrophic factor (BDNF) (Koike et al, Behavioural Brain Research 238:48-52, 2013). Since BDNF and other growth factors have been shown to be critically involved mediating synaptic plasticity, this mechanism is likely to contribute to both antidepressant and procognitive properties of these compounds. Inhibition of mGluRs of the group-II receptor family is therefore considered to represent a potential therapeutic mechanism for neurological disorders, including depression and cognitive or memory dysfunction.

Positron Emission Tomography (PET) is a non-invasive imaging technique that offers the highest spatial and temporal resolution of all nuclear imaging techniques and has the added advantage that it can allow for true quantification of tracer concentrations in tissues. It uses positron emitting radionuclides such as, for example, $^{15}$O, $^{13}$N, $^{11}$C and $^{18}$F for detection. Several positron emission tomography radiotracers have been reported so far for in vivo imaging of mGluRs. There is still a need to provide improved positron emission tomography radiotracers for imaging Group II mGlu receptors.

SUMMARY OF THE INVENTION

The present invention relates to a compound having the Formula (I)

wherein at least one atom is radioactive, or a pharmaceutically acceptable salt or a solvate thereof.

In a particular embodiment, the compound of Formula (I) is compound 1 compound 1 or a pharmaceutically acceptable salt or a solvate thereof.

The invention also relates to precursor compounds for the synthesis of compound 1. Thus, the present invention also relates to compounds of Formulae P-1, P-2 and P-3

P-1

P-2

P-3 or a pharmaceutically acceptable salt or a solvate thereof.

A particular pharmaceutically acceptable salt of P-2 is the methylsulfonate salt.

The invention also relates to a pharmaceutical composition comprising a compound of Formula (I) or a pharmaceutically acceptable salt thereof and a pharmaceutically acceptable carrier or diluent. In a particular embodiment, said pharmaceutical composition is particularly suitable for diagnosis and may be referred to therefore as a diagnostic pharmaceutical composition. In particular, said pharmaceutical composition is a sterile solution. Thus, illustrative of the invention is a sterile solution comprising a compound of Formula (I) described herein.

The invention further relates to the use of a compound of Formula (I) as an imaging agent. Therefore, exemplifying the invention is a use of a compound of Formula (I) as described herein, for, or a method of, imaging a tissue, cells or a mammal, in vitro or in vivo. In particular, the invention relates to a compound of Formula (I) as described herein, for use as a contrast agent for imaging a tissue, cells or a mammal, in vitro, ex vivo, or in vivo. The invention further relates to a composition comprising a compound of Formula (I) for use as a contrast agent for imaging a tissue, cells or a mammal, in vitro, ex vivo, or in vivo.

The invention also relates to a method for imaging a tissue, cells or a mammal, comprising contacting with or providing or administering a detectable amount of a labelled compound of Formula (I) as described herein to a tissue, cells or a mammal, and detecting the compound of Formula (I).

Further exemplifying the invention is a method of imaging a tissue, cells or a mammal, comprising contacting with or providing or administering to a tissue, cells or a mammal, a compound of Formula (I) as described herein, and imaging the tissue, cells or mammal with a positron-emission tomography imaging system. Additionally, the invention refers to a process for the preparation of a compound according to Formula (I) as described herein, comprising

(a) the steps of (a-1) reacting a compound of Formula (P-1) with methanesulfonic anhydride in the presence of a base and an inert solvent, for example, trimethylamine or triethylamine and dichloromethane, and (a-2) reacting the compound obtained in step (a-1) with a nucleophilic radioactive fluorinating reagent $[^{18}F]F^-$ in the presence of a base in an inert solvent (b) the step of reacting a compound of Formula (P-2) with a nucleophilic radioactive fluorinating reagent [$^{18}$F]F$^-$ in the presence of a base in an inert solvent (c) the step of reacting a compound of Formula (P-3) with a nucleophilic radioactive fluorinating reagent [$^{18}$F]F$^-$ in the presence of a base in an inert solvent Suitable nucleophilic radioactive fluorinating reagents in steps (a-2), (b) and (c) are, for instance, K[$^{18}$F]/Kryptofix 222 or tetraalkylammonium salts incorporating radioactive fluoride [$^{18}$F]F. Suitable bases in steps (a-2), (b) and (c), are, for instance K$_2$CO$_3$ or Cs$_2$CO$_3$. Suitable solvents in steps (a-2), (b) and (c), are, for instance, DMSO, CH$_3$CN or DMF, optionally with the addition of a small amount of water.

DESCRIPTION OF THE FIGURES

FIG. 2 shows the time activity curves for the uptake of [$^{18}$F]-1 with and without pretreatment of 10 mg/kg compound A (a NAM compound, selective for mGlu2/3 (~20 fold selective for 2 over 3) vs other mGluRs), indicated in the figure as mGlu2/3 NAM in SD rats, wherein

| + Pons pretreated | ♦ Pons | x Frontal Cortex |
|---|---|---|
| x Hippocampus | ○ Striatum | ◇ Frontal cortex pretreated |
| □ Hippocampus pre-treated | △ Striatum pretreated | |

| ■ Frontal | ▲ Hippocampus | x Cerebellum |
|---|---|---|
| * Pons | + Frontal pretreated | - Hippocampus pretreated |
| ● Cerebellum pretreated | ♦ Pons pretreated | |

| ♦ Whole brain | ■ Frontal lobe | ▲ Cerebellum |
|---|---|---|
| x Hippocampus | * Pons | |

DETAILED DESCRIPTION OF THE INVENTION

As already mentioned, the compound of Formula (I) and compositions comprising the compounds of Formula (I) can be used for imaging a tissue, cells or a mammal, in vitro or in vivo. In particular, the invention relates to a method of imaging or quantifying the mGlu2 and 3 receptors in a tissue, cells or a mammal in vitro or in vivo.

The cells and tissues are preferably central nervous system cells and tissues in which the mGlu2 and 3 receptors are abundant. As already mentioned, the mGlu2 and 3 receptors are abundant in central nervous system tissue, more in particular, in central nervous system tissue forming the brain; more in particular, forming the cerebral cortex, thalamic regions, accessory olfactory bulb, hippocampus, amygdala, caudate-putamen and nucleus accumbens.

When the method is performed in vivo, the compound of Formula (I) can be administered intravenously, for example, by injection with a syringe or by means of a peripheral intravenous line, such as a short catheter.

When the mammal is a human, the compound of Formula (I) or a sterile solution comprising a compound of Formula (I), may in particular be administered by intravenous administration in the arm, into any identifiable vein, in particular in the back of the hand, or in the median cubital vein at the elbow.

Thus, in a particular embodiment, the invention relates to a method of imaging a tissue or cells in a mammal, comprising the intravenous administration of a compound of Formula (I), as defined herein, or a composition comprising a compound of Formula (I) to the mammal, and imaging the tissue or cells with a positron-emission tomography imaging system.

Thus, in a further particular embodiment, the invention relates to a method of imaging a tissue or cells in a human, comprising the intravenous administration of a compound of Formula (I), as defined herein, or a sterile formulation comprising a compound of Formula (I) to the human, and imaging the tissue or cells with a positron-emission tomography imaging system.

In a further embodiment, the invention relates to a method of imaging or quantifying the mGlu2 and 3 receptors in a mammal, comprising the intravenous administration of a compound of Formula (I), or a composition comprising a compound of Formula (I) to the mammal, and imaging with a positron-emission tomography imaging system.

In another embodiment, the invention relates to the use of a compound of Formula (I) for imaging a tissue, cells or a mammal, in vitro or in vivo, or the invention relates to a compound of Formula (I), for use in imaging a tissue, cells or a mammal in vitro or in vivo, using positron-emission tomography.

The invention also relates to a method for imaging or quantifying the mGlu2 and 3 receptors in a mammal, the method comprising providing a detectable amount of a compound of Formula (I) to a mammal and detecting the compound of Formula (I) associated with mGlu2 and 3 receptors. The method also allows for determining mGlu2 and 3 receptor occupancy by other non-radiolabelled compounds, therefore, the invention relates to the compound of Formula (I) as defined herein, or the pharmaceutical composition according to the invention, for use in determining mGlu2 and 3 receptor site occupancy by other non-radiolabelled compounds.

Furthermore, the invention relates to a method of assessing a disorder or predisposition thereto related to the mGlu2 and 3 receptors in a subject, the method comprising providing a detectable amount of a compound of Formula (I) or pharmaceutical composition according to the invention, wherein the compound of Formula (I) passes the blood-brain barrier and preferentially binds to mGlu2 and 3 receptors in brain tissue, allowing the compound to distribute into the brain tissue, and imaging the brain tissue.

The compound is provided to a subject in a detectable amount and after sufficient time has passed for the compound to become associated with the mGlu2 and 3 receptors, the labelled compound is detected noninvasively.

Definitions

As used herein, the term "composition" is intended to encompass a product comprising the specified ingredients in the specified amounts, as well as any product which results, directly or indirectly, from combinations of the specified ingredients in the specified amounts.

The term "detectable amount" refers to the concentration of compound above the lowest limit of detection of the imaging instrument, in particular, of the PET scanning instrument.

The absolute configuration is specified according to the Cahn-Ingold-Prelog system.

Addition salts of the compounds according to the invention also intended to be encompassed within the scope of this invention.

Acceptable salts of the compounds of the invention are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention. The pharmaceutically acceptable salts are defined to comprise the therapeutically active non-toxic acid addition salt forms that the compounds according to the invention are able to form. Said salts can be obtained by treating the base form of the compounds according to the invention with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzensulfonic acid, p-toluenesulfonic acid, cyclamic acid, salicylic acid, p-aminosalicylic acid and pamoic acid.

Conversely, said salt forms can be converted into the free base form by treatment with an appropriate base.

In addition, some of the compounds of the present invention may form solvates with water (i.e., hydrates) or common organic solvents, and such solvates are also intended to be encompassed within the scope of this invention.

The term "subject" as used herein, refers to an animal, preferably a mammal, most preferably a human, who is or has been the object of treatment, observation or experiment. Unless otherwise stated, "subject" includes both, healthy animals and animals afflicted by different diseases or disorders.

The term "mammal" refers, in particular to humans, mice, dogs and rats.

The term "cell" refers to a cell expressing or incorporating the mGlu2 and/or 3 receptors.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006).

Applications

The compounds according to the present invention find various applications for imaging tissues, cells or a mammal, both in vitro and in vivo. Thus, for instance, they can be used to map the differential distribution of mGluR2/3 in subjects of different age and sex. Further, they allow one to explore for differential distribution of mGluR2/3 in subjects afflicted by different diseases or disorders. Thus, abnormal distribution may be helpful in diagnosis, case finding, stratification of subject populations, and in monitoring disease progression in individual subjects. The radioligands may further find utility in determining mGluR2/3 site occupancy by other ligands. Since the radioligand is administered in trace amounts, i.e. in detectable amounts for example for PET imaging, no therapeutic effect may be attributed to the administration of the radioligands according to the invention.

Experimental Part

Preparation of the Intermediates, [¹⁹F]-Compound 1 and Precursors

General

As used herein, the term "aq." means aqueous, "DCM" means dichloromethane, "DIPE" means diisopropyl ether, "DMF" means N,N-dimethylformamide, "DMSO" means dimethyl sulfoxide, "DSC" means differential scanning calorimetry, "Et₃N/TEA" means triethylamine, "EtOH" means ethanol, "EtOAc" means ethyl acetate, "eq." means equivalent(s), "h" means hours, "HPLC" means high-performance liquid chromatography, "LCMS" means liquid chromatography/mass spectrometry, "[M+H]⁺" means the protonated mass of the free base of the compound, "[M−H]⁻" means the deprotonated mass of the free base of the compound, "min" means minutes, "m.p." means melting point, "mw/MW" means microwave, "quant." means quantitative, "r.m." means reaction mixture, "r.t./RT" means room temperature" "$R_t$," means retention time (in minutes), "sat." means saturated, "sol." means solution, "THF" means tetrahydrofuran, "UV" means ultraviolet.

Microwave assisted reactions were performed in a single-mode reactor: Biotage Initiator™ Sixty microwave reactor (Biotage).

Thin layer chromatography (TLC) was carried out on silica gel 60 F254 plates (Merck) using reagent grade solvents. Open column chromatography was performed on silica gel, mesh 230-400 particle size and 60 Å pore size (Merck) under standard techniques. Automated flash column chromatography was performed using ready-to-connect cartridges from Merck, on irregular silica gel, particle size 15-40 μm (normal phase disposable flash columns) on an SPOT or LAFLASH system from Armen Instrument.

Several methods for preparing the compounds of this invention are illustrated in the following examples, which are intended to illustrate but not to limit the scope of the present invention. Unless otherwise noted, all starting materials were obtained from commercial suppliers and used without further purification.

Preparation of Intermediate Compounds

Intermediate 1 (I-1)

Copper(I) iodide (25.20 g, 132.30 mmol) was added to a stirred suspension of (7S)-6,7-dihydro-7-methyl-pyrazolo[1,5-a]pyrazin-4(5H)-one([1639901-79-3], WO2014195311, 50.00 g, 330.76 mmol), 5-bromo-2-(trifluoromethyl)benzyl alcohol (84.35 g, 330.76 mmol), K₂CO₃ (91.43 g, 661.52 mmol) and N,N'-dimethylethylene-diamine (16.73 mL, 132.30 mmol) in toluene (439 mL) under nitrogen. The mixture was stirred at 105° C. for 18 h. Then the mixture was diluted with water and NH₃ (32%) and extracted with DCM. The organic layer was separated, dried (Na₂SO₄), filtered and the solvents evaporated in vacuo. The crude product was purified by open column chromatography (silica; EtOAc/heptane 30/70 to 75/25). The desired fractions were collected and concentrated in vacuo. The product was precipitated in EtOAc/heptane mixture. Filtration and drying yielded I-1 (72.7 g, 68%) as a white solid.

Intermediate 2 (I-2)

Iodine (39.65 g, 156.23 mmol) was added to a solution of I-1 (72.60 g, 223.19 mmol) and ammonium cerium(IV) nitrate (85.65 g, 156.23 mmol) in CH₃CN (750 mL) and the mixture was stirred at 75° C. for 45 min. Then the mixture was cooled to r.t., diluted with EtOAc and washed with diluted Na₂S₂O₃. The organic layer was separated, dried (Na₂SO₄), filtered and the solvents evaporated in vacuo. The crude product was purified by flash column chromatography (silica; EtOAc/heptane 20/80 to 40/60). The desired fractions were collected and evaporated in vacuo to give I-2 (85.50 g, 85%) as a white foam.

Intermediate 3 (I-3)

Bis(2-methoxyethyl)amino-sulfur trifluoride (55.57 mL, 150.71 mmol) was added to a stirred solution of intermediate I-2 (40.00 g, 88.66 mmol) in DCM (400 mL) at 0° C. and under nitrogen. The mixture was allowed to warm up to rt and stirred at rt for 1 h. Then it was treated with a sat. aq. sol. NaHCO₃ at 0° C. and then at r.t. and extracted with DCM. The organic layer was separated, dried (Na₂SO₄), filtered and concentrated in vacuo. The crude product was purified by flash column chromatography (silica; eluent DCM). The desired fractions were collected and concentrated in vacuo to yield intermediate compound I-3 (25.00 g, 62%) as a white solid.

Preparation of Compound [19F]-1

Copper(I) iodide (4.12 g, 21.63 mmol) was added to a deoxygenated stirred suspension of I-3 (24.50 g, 54.06 mmol), 2-aminopyridine-3-carboxamide (11.12 g, 81.09 mmol) and K₃PO₄ (34.43 g, 162.19 mmol) in 1,4-dioxane (600 mL) under nitrogen. Then (+/−)-trans-1,2-cyclohexanediamine (2.60 mL) was added and the mixture was stirred for 16 h at 100° C. After cooling to RT the r.m. was filtered and washed with EtOAc. The filtrate was washed with diluted aq. NH3 solution, separated, dried (Na₂SO₄), filtered and the solvents evaporated in vacuo. The crude product was purified by open column chromatography (silica; EtOAc in heptane 50/50 to 100/0). The desired fractions were collected and concentrated in vacuo. Impure fractions were further purified by flash column chromatography (silica; MeOH/DCM 0/100 to 2/98). All desired fractions from both columns were combined and evaporated in vacuo. This product was crystallized in isopropanol (20 Volumes). Filtration and drying in vacuo at 50° C. yielded [19F]-1 (14.48 g, 58%) as an off white solid.

Preparation of Precursor 1 (P-1)

Copper(I) iodide (5.07 g, 26.60 mmol) was added to a deoxygenated stirred suspension of I-2 (30 g, 66.49 mmol), 2-aminopyridine-3-carboxamide (13.68 g, 99.74 mmol) and K₃PO₄ (42.34 g, 199.47 mmol) in 1,4-dioxane (600 mL) under nitrogen. Then (+/−)-trans-1,2-cyclohexanediamine (3.20 mL, 26.60 mmol) was added and the mixture was stirred for 18 h at 100° C. The mixture was filtered and rinsed with DCM. The solution was further diluted with DCM and washed with diluted NH3 solution. The organic phase was dried (Na₂SO₄), filtered and evaporated in vacuo. The crude product was purified by flash column chromatography (silica; EtOAc/heptane 50/50 to 80/20). The desired fractions were collected and evaporated in vacuo to yield a product which was further purified by flash column chromatography (silica; 7N NH3 in MeOH/DCM 0/100 to 1.5/98.5). The desired fractions were collected and evaporated in vacuo, resulting in a product which was precipitated in DIPE. The precipitate was filtered and dried in vacuo at 50° C. to yield P-1 (20.51 g, 67%) as a white solid.

Preparation of Precursor 2 (P-2)

To a mixture of P-1 (15.00 g, 32.58 mmol) and DCM (400 mL) was added TEA (7.25 mL, 52.13 mmol). The mixture was cooled to 0° C. and then methanesulfonic anhydride (8.51 g, 48.87 mmol) in DCM (50 mL) was added. The mixture was stirred at 0° C. for 3 h. Then methanesulfonic acid (2.54 mL) in water (300 mL) was added and stirred for 30 min. Then the DCM was partially evaporated in vacuo. Then NaHCO₃ (7.5 g) was added and the mixture was extracted with EtOAc. The aqueous layer was removed, and the organic layer washed with sat. NaHCO₃, then dried (Na₂SO₄) and filtered. Methanesulfonic acid (2.54 mL, 39.10 mmol) was then added and the mixture was evaporated to dryness. The residue was treated with diethyl ether and the precipitated product was filtered. The resulting solid was crystallized in CH₃CN (15 Volumes). The compound was filtered, and dried overnight in vacuo at 50° C., resulting in P-2 (12.9 g, 62%) as a light yellow solid.

Preparation of Precursor 3 (P-3)

Phosphorus tribromide (1 M in DCM, 0.40 mL, 0.40 mmol) was added to a stirred solution of P-1 (61.8 mg, 0.13 mmol) in DCM (2.4 mL) under nitrogen. The mixture was stirred at r.t. for 1 h. Then the mixture was stirred at 80° C. for 5 min under microwave irradiation. Subsequently, additional phosphorus tribromide (1M in DCM, 0.08 mL, 0.08 mmol) was added and the mixture was stirred at 80° C. for 5 min under microwave irradiation. The mixture was then diluted with DCM, cooled to 0° C. and treated with sat. NaHCO₃. The organic layer was separated, dried (Na₂SO₄), filtered, diluted with heptane and evaporated in vacuo to yield P-3 (39 mg, 56%) as a white solid.

Preparation of Compound [$^{18}$F]-1

General

Chemicals were obtained from Sigma-Aldrich (Saint Louis, USA) and were used without further purification. [$^{18}$F]F$^-$ was produced by an IBA Cyclone 18/9 cyclotron (Louvain-la-Neuve, Belgium). Preparative HPLC was performed on an Xbridge C18 column (4.6×250 mm, 5 µm; Waters, Milford USA), using EtOH/0.01 M phosphate buffer in water pH 7.4 (39/61 v/v) at flow rate 1 mL·min$^{-1}$ and wavelength of 254 nm (method A).

The identity of the radiotracers was confirmed using the same analytical HPLC methods as described above after co-injection with their non-radioactive analogue. Millex GV filters were obtained from Millipore (Amsterdam, The Netherlands). Radioactivity was counted using the Wizard 1480 automated gamma counter (Perkin Elmer, Waltham, USA).

Radiosynthesis of Compound 1 ([$^{18}$F]-1)

Synthesis of [$^{18}$F]-1 via the Alcohol Precursor (P-1)

For the synthesis of [$^{18}$F]-1 according to this procedure, the corresponding alcohol precursor was mesylated immediately prior to radiosynthesis according to the following protocol: ~7.5 mg P-1 (1 eq) was dissolved in DCM (2 mL), then trimethylamine (2.5 µL, 1.1 eq) was added, followed by the addition of methanesulfonic anhydride (3.5 mg, 1.1 eq) and the mixture was incubated for 60 min at r.t. Then the r.m. was washed with water (2×) and dried over MgSO$_4$, filtered and evaporated to dryness at 30° C. in vacuo. Hereafter the product was azeotropically dried using CH$_3$CN (3×2 mL) also at 30° C. in vacuo. After evaporation of the last portion of CH$_3$CN, the mesylated precursor was ready for use. TLC (silica plates eluted with 95% DCM and 5% MeOH) were used to check the purity of the corresponding precursor.

[$^{18}$F]F$^-$ was collected by purging the proton irradiated target content (98% $^{18}$O—H$_2$O) over a QMA (Waters, Milford USA) cartridge. Next the QMA cartridge was eluted, using CH$_3$CN/water (700 µL of 95/5 v/v) containing Kryptofix 222 (26 mg) and K$_2$CO$_3$ (2.5 mg) to the reaction vial. The solution was dried under a gentle helium flow at 110° C. for 6 min, followed twice by addition of CH$_3$CN (1 mL) and dried under helium at 110° C. for 5 min each. For the standard conditions: the mesyl precursor (2 mg, 3.7 µmol) in dry DMSO (0.5 mL) was added, and reacted for 10 min at 120° C. The r.m. was diluted and [$^{18}$F]-1 was subsequently purified using HPLC method A. The collected fraction was then passed over a sterile millex GV filter, and was further diluted with saline to a concentration of 10% EtOH.

Synthesis of [$^{18}$F]-1 via the Mesylated Salt (P-2.CH$_3$SO$_2$OH) or via the Bromo Precursor (P-3).

[$^{18}$F]F$^-$ was collected by purging the irradiated target content over a QMA (Waters, Milford USA) cartridge. Next the QMA cartridge was eluted, using CH$_3$CN/water (700 µL of 95/5 v/v) containing Kryptofix 222 (26 mg) and K$_2$CO$_3$ (2.5 mg) to the reaction vial. The solution was dried under a gentle helium flow at 110° C. for 6 min, followed twice by an addition of CH$_3$CN (1 mL) and dried under helium at 110° C. for 5 min each. For the standard conditions: the mesyl or the bromo precursor (2 mg) in dry DMSO (0.5 ml) was added, and reacted for 10 min at 120° C. The r.m. was diluted and [$^{18}$F]-1 was subsequently purified on an Xbridge C18 column (4.6×250 mm, 5 µm; Waters, Milford USA), using EtOH/0.01 M phosphate buffer in water pH 7.4 (39/61 v/v) at flow rate 1 mL·min–1 and wavelength 254 nm. [$^{18}$F]-1 was then collected (~26 min retention time) and the collected fraction was then passed over a sterile millex GV filter, and was further diluted with saline so that the product contained 10% EtOH. The radiochemical yield was 35-60% of [$^{18}$F]-1 (N=4) (decay corrected) from the mesyl precursor, and ~35% (N=2) (decay corrected) from the bromo precursor.

Analytical Part

Melting Points

Values are peak values, and are obtained with experimental uncertainties that are commonly associated with this analytical method.

DSC823e (A): For a number of compounds, melting points were determined with a DSC823e (Mettler-Toledo) apparatus. Melting points were measured with a temperature gradient of 10° C./minute. Maximum temperature was 300° C. Values are peak values.

Mettler Toledo Mettler FP 81HT/FP90 apparatus (B): For a number of compounds, melting points were determined in open capillary tubes on a Mettler FP 81HT/FP90 apparatus. Melting points were measured with a temperature gradient of 1, 3, 5 or 10° C./minute. Maximum temperature was 300° C. The melting point was read from a digital display.

LCMS

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW) and/or exact mass monoisotopic molecular weight. Data acquisition was performed with appropriate software.

Compounds are described by their experimental retention times (R$_t$) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, [M+CH$_3$COO]$^-$ etc. . . . ). For molecules with multiple isotopic patterns (Br, Cl, . . . ), the reported value is the one obtained for the lowest isotope mass. All results were obtained with experimental uncertainties that are commonly associated with the method used.

Hereinafter, "SQD" Single Quadrupole Detector, "MSD" Mass Selective Detector, "QTOF" Quadrupole-Time of Flight, "rt" room temperature, "BEH" bridged ethylsiloxane/silica hybrid, "CSH" charged surface hybrid, "UPLC" Ultra Performance Liquid Chromatography, "DAD" Diode Array Detector.

TABLE 1

LC-MS Methods (Flow expressed in mL/min; column temperature (T) in ° C; Run time in min).

| Method | Instrument | Column | Mobile phase | Gradient | Flow Col T | Run time |
|---|---|---|---|---|---|---|
| 1 | Waters: Acquity® UPLC® - DAD/SQD | Waters: CSH™ C18 (1.7 µm, 2.1 x 50 mm) | A: 95% CH$_3$COONH$_4$ 6.5 mM + 5% CH$_3$CN, B: CH$_3$CN | From 95% A to 40% A in 1.2 min, to 5% A in 0.6 min, held for 0.2 min | 1 50 | 5 |

TABLE 1-continued

LC-MS Methods (Flow expressed in mL/min; column temperature (T) in ° C; Run time in min).

| Method | Instrument | Column | Mobile phase | Gradient | Flow Col T | Run time |
|---|---|---|---|---|---|---|
| 2 | Waters: Acquity ® IClass UPLC ®- DAD/Xevo G2-S QTOF | Waters: BEH C18 (1.7 μm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | 1 50 | 5 |

(*) Different MS tuning parameters (due to low sensitivity or ionization mode)

TABLE 2

Analytical data—melting point (M.p.) and LCMS:
$[M + H]^+$ means the protonated mass of the free base of the compound, $[M - H]^-$ means the deprotonated mass of the free base of the compound or the type of adduct specified $[M + CH_3COO]^-$). $R_t$ means retention time (in min). For some compounds, exact mass was determined.

| Co. No. | M.p. ° C. | $[M + H]^+$ | $R_t$ | LCMS Method |
|---|---|---|---|---|
| [$^{19}$F]-1 | 150.62 (A)* | 463 | 2.22 | 2 |
| P-1 | n.d. | 461 | 1.76 | 2 |
| P-3 | n.d. | 523 | 1.33 | 1 |
| P-2 | n.d. | 539 | 1.98 | 2 | n.d. means not determined.
*other minor crystalline form detected, reported only the highest value.

Optical Rotations

Optical rotations were measured on a Perkin-Elmer 341 polarimeter with a sodium lamp and reported as follows: $[\alpha]^\circ$ ($\lambda$, c g/100 ml, solvent, T ° C.).

$[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 mL).

TABLE 3

Optical Rotation data.

| Co. No. | $\alpha_D(°)$ | Wavelength (nm) | Concentration w/v % | Solvent | Temp. ° C. |
|---|---|---|---|---|---|
| [$^{19}$F]-1 | +31.3 | 589 | 0.51 | DMF | 20 |
| P-1 | +29.2 | 589 | 0.63 | DMF | 20 |

NMR

For a number of compounds, $^1$H NMR spectra were recorded on a Bruker DPX-400 spectrometer operating at 400 MHz or on a Bruker Avance I spectrometer operating at 500 MHz, using CHLOROFORM-d (deuterated chloroform, CDCl$_3$) or DMSO-d$_6$ (deuterated DMSO, dimethyl-d6 sulfoxide) as solvent. Chemical shifts (δ) are reported in parts per million (ppm) relative to tetramethylsilane (TMS), which was used as internal standard.

TABLE 4

$^1$H NMR results

| Co. No. | $^1$H NMR result |
|---|---|
| P-1 | $^1$H NMR (400 MHz, CDCl$_3$) δ ppm 1.71 (d, J = 6.5 Hz, 3 H) 2.90 (br s, 1 H) 4.01 (dd, J = 12.6, 8.2 Hz, 1 H) 4.20 (dd, J = 12.7, 4.2 Hz, 1 H) 4.64-4.74 (m, 1 H) 4.96 (s, 2 H) 6.56 (dd, J = 7.9, 4.9 Hz, 1 H) 6.58 (br s, 2 H) 7.39 (dd, J = 8.3, 1.4 Hz, 1 H) 7.72 (d, J = 8.6 Hz, 1 H) 7.76 (dd, J = 7.9, 1.6 Hz, 1 H) 7.79-7.82 (m, 1 H) 8.15 (dd, J = 4.9, 1.6 Hz, 1 H) 8.38 (s, 1 H) 9.71 (s, 1 H) |
| P-2 | $^1$H NMR (500 MHz, DMSO-d$_6$) δ ppm 1.58 (d, J = 6.4 Hz, 3 H) 2.37 (s, 3 H) 3.31 (s, 3 H) 4.16 (dd, J = 12.7, 8.4 Hz, 1 H) 4.38 (dd, J = 12.7, 4.0 Hz, 1 H) 4.77-4.85 (m, 1 H) 5.41 (s, 2 H) 7.01 (dd, J = 7.7, 6.2 Hz, 1 H) 7.73 (dd, J = 8.5, 1.3 Hz, 1 H) 7.87 (d, J = 1.7 Hz, 1 H) 7.93 (d, J = 8.7 Hz, 1 H) 8.20 (dd, J = 6.1, 1.4 Hz, 1 H) 8.31 (br s, 4 H) 8.34 (dd, J = 7.7, 1.6 Hz, 1 H) 10.15 (s, 1 H) |
| P-3 | $^1$H NMR (400 MHz, CDCl$_3$) δ ppm 1.74 (d, J = 6.5 Hz, 3 H) 4.04 (dd, J = 12.6, 8.2 Hz, 1 H) 4.22 (dd, J = 12.6, 4.3 Hz, 1 H) 4.67 (s, 2 H) 4.68-4.78 (m, 1 H) 6.57 (br s, 2 H) 6.61 (dd, J = 7.9, 4.9 Hz, 1 H) 7.45 (dd, J = 8.3, 1.2 Hz, 1 H) 7.64 (d, J = 1.6 Hz, 1 H) 7.76 (d, J = 8.6 Hz, 1 H) 7.79 (dd, J = 7.9, 1.6 Hz, 1 H) 8.20 (dd, J = 4.6, 1.6 Hz, 1 H) 8.42 (s, 1 H) 9.70 (s, 1 H) |
| [$^{19}$F]-1 | $^1$H NMR (500 MHz, CDCl$_3$) δ ppm 1.72 (d, J = 6.4 Hz, 3 H) 4.03 (dd, J = 12.4, 8.1 Hz, 1 H) 4.22 (dd, J = 12.4, 4.3 Hz, 1 H) 4.64-4.76 (m, 1 H) 5.66 (d, J = 46.5 Hz, 2 H) 6.55-6.62 (m, 3 H) 7.49 (d, J = 8.4, 0.9 Hz, 1 H) 7.68 (s, 1 H) 7.77 (d, J = 7.8 Hz, 1 H) 7.78 (d, J = 7.8 Hz, 1 H) 8.18 (dd, J = 4.9, 1.7 Hz, 1 H) 8.41 (s, 1 H) 9.70 (s, 1 H). |

Binding Assay

For [$^3$H]-compound A (a NAM compound, selective for mGlu2/3 (~20 fold selective for 2 over 3) vs other mGluRs) binding, membranes from human mGlu2 and mGlu3 HEK293 cells, and also rat cortical membranes, were used. After thawing, membranes were homogenized using an Ultra Turrax homogenizer and suspended in ice-cold binding buffer containing 50 mM Tris-HCl (pH 7.4), 10 mM MgCl$_2$, 2 mM CaCl$_2$. Displacement studies were done using 6 nM of radioligand, except for human mGlu3 membranes where 25 nM was used. Assay mixtures were incubated for 60 min at RT in a volume of 0.5 ml containing 7.5 mg, 75-100 mg or 75 µg membrane protein of human mGlu2, human mGlu3 or rat cortex, respectively. Non-specific binding was estimated in the presence of 10 mM compound B (a NAM with $IC_{50}$~10 nM against hmGlu2 and $IC_{50}$~200 nM against hmGlu3). Filtration was performed using Whatman GF/C filter sheets pre-soaked in 0.1% PEI and a Brandell harvester 96.

Filters from filters sheets were punched into vials. After the addition of scintillation liquid, radioactivity on the filters was counted in a Liquid Scintillation Analyzer from Perkin Elmer.

Radioligand competition binding data were calculated as percentage of total binding measured in the absence of test compound. Inhibition curves, plotting percentage of total binding versus the log concentration of the test compound, were generated using the Lexis software. Sigmoid inhibition curves were analyzed using non-linear regression analysis.

TABLE 5

Binding data for compound 1.

| Protocol | pIC$_{50}$ | Eff Curve |
|---|---|---|
| mGlu2 HEK293 | 8.54 | 85 |
| mGlu3 HEK293 | 8.3 | 96 |
| mGlu2-3 rat cortex | 8.7 | 103 |

Biodistribution Studies—Sprague-Dawley Rats

Animal PET imaging was performed on a lutetium oxyorthosilicate detector-based tomograph (microPET FOCUS-220; Siemens Medical Solutions USA, Knoxville, Tenn.), which had a transaxial resolution of 1.35 mm (full-width at half-maximum). Data were acquired in a 128×128×95 matrix with a pixel width of 0.475 mm and a slice thickness of 0.796 mm. During PET imaging, rats were kept under gas anesthesia (2.5% isoflurane in oxygen at a flow rate of 1 l/min), and their body temperature was maintained between 36.5 and 37° C. using a heating pad. PET data were analyzed using Pmod software version 3.2 (Pmod, Zurich Switzerland).

Sprague-Dawley rats obtained from Harlan (the Netherlands), were housed in groups of four to six per cage until treatment. They were kept at a constant temperature of 21° C. and at a 12-h light/dark cycle, in which lights were switched on at 8:00 a.m. Animals had unrestricted access to food (Teklad Global 16% Protein Rodent Diet, Harlan, Madison, Wis., USA) and water. All animal experiments were performed in compliance with Belgium laws on animal experimentation and after approval by the local animal ethics committee.

General Method

Ex-Vivo Biodistribution

The biodistribution of [$^{18}$F]-1 was determined at 2, 10, 30 and 60 min, after injection in Sprague Dawley rats (n=3 per time point. Rats were injected intravenously with 0.7-1.1 MBq via a tail vein and euthanized at the time points indicated above, under isoflurane anesthesia. All tissues were dissected, weighed and counted for radioactivity in a gamma counter.

The biodistribution of [$^{18}$F]-1 showed a high initial uptake in liver, kidneys, pancreas and heart, followed by a fast washout. Blood uptake was low, with a slow washout. Bone uptake was slightly going up over time, while the low muscle uptake which peaked after 10 minutes was followed by a slow washout.

The brain uptake of [$^{18}$F]-1 was high, with the highest uptake in the cerebral cortex, and the lowest uptake in the pons. All brain areas except for the pons showed the highest uptake around 10 min, followed by a fast washout, while the pons peaked at 2 minutes, followed by a fast washout.

TABLE 6

Uptake of [$^{18}$F]-1 in SUV ± SD

| Organ | Mean 2 min | SD | Mean 10 min | SD | Mean 30 min | SD | Mean 60 min | SD |
|---|---|---|---|---|---|---|---|---|
| kidneys | 6.59 | 0.51 | 2.76 | 0.15 | 2.24 | 0.56 | 1.87 | 0.06 |
| liver | 8.81 | 0.34 | 5.70 | 0.17 | 3.90 | 0.71 | 2.42 | 0.05 |
| spleen | 3.71 | 0.37 | 1.64 | 0.15 | 1.13 | 0.27 | 0.87 | 0.08 |
| pancreas | 6.47 | 1.02 | 3.07 | 0.29 | 2.84 | 0.55 | 2.75 | 0.04 |
| lungs | 4.70 | 1.23 | 2.27 | 0.09 | 2.01 | 0.50 | 1.77 | 0.14 |
| heart | 4.73 | 0.36 | 2.16 | 0.07 | 1.49 | 0.39 | 1.14 | 0.34 |
| striatum | 3.21 | 0.10 | 3.56 | 0.61 | 3.03 | 0.74 | 1.14 | 0.28 |
| hippo-campus | 2.49 | 0.17 | 2.83 | 0.10 | 1.94 | 0.52 | 0.80 | 0.13 |
| pons | 2.65 | 0.08 | 2.13 | 0.13 | 1.29 | 0.35 | 0.56 | 0.03 |
| cortex | 5.42 | 0.58 | 5.98 | 0.25 | 3.87 | 1.35 | 1.36 | 0.44 |
| rest of cerebrum | 3.24 | 0.20 | 3.74 | 0.45 | 2.45 | 0.92 | 0.91 | 0.17 |
| whole cerebrum | 3.11 | 0.11 | 3.43 | 0.23 | 2.31 | 0.77 | 0.87 | 0.15 |
| cerebellum | 3.42 | 0.14 | 3.33 | 0.33 | 1.90 | 0.57 | 0.72 | 0.16 |
| blood | 0.72 | 0.08 | 0.50 | 0.02 | 0.39 | 0.08 | 0.28 | 0.02 |
| cerebrum + cerebellum | 3.19 | 0.08 | 3.45 | 0.25 | 2.28 | 0.74 | 0.85 | 0.15 |
| bone | 0.61 | 0.07 | 0.52 | 0.02 | 0.73 | 0.44 | 0.67 | 0.11 |
| muscle | 0.57 | 0.11 | 1.07 | 0.12 | 0.87 | 0.23 | 0.65 | 0.05 |

PET Scanning

Figure 1A:
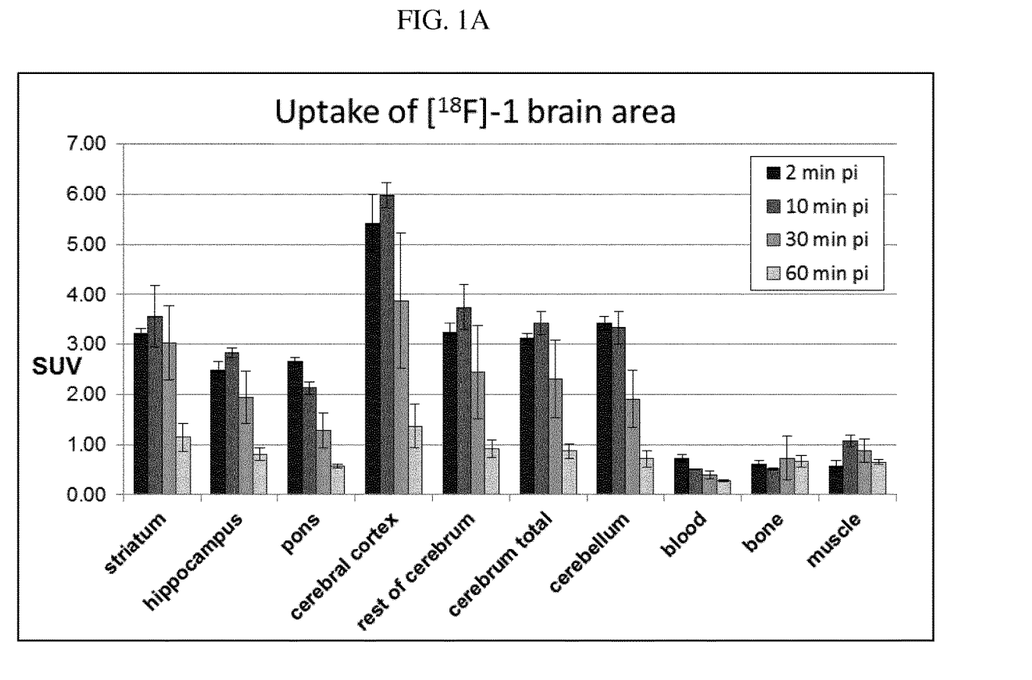
FIG. 1a shows the biodistribution of [$^{18}$F]-1 in brain in SD rats.
Figure 1B:
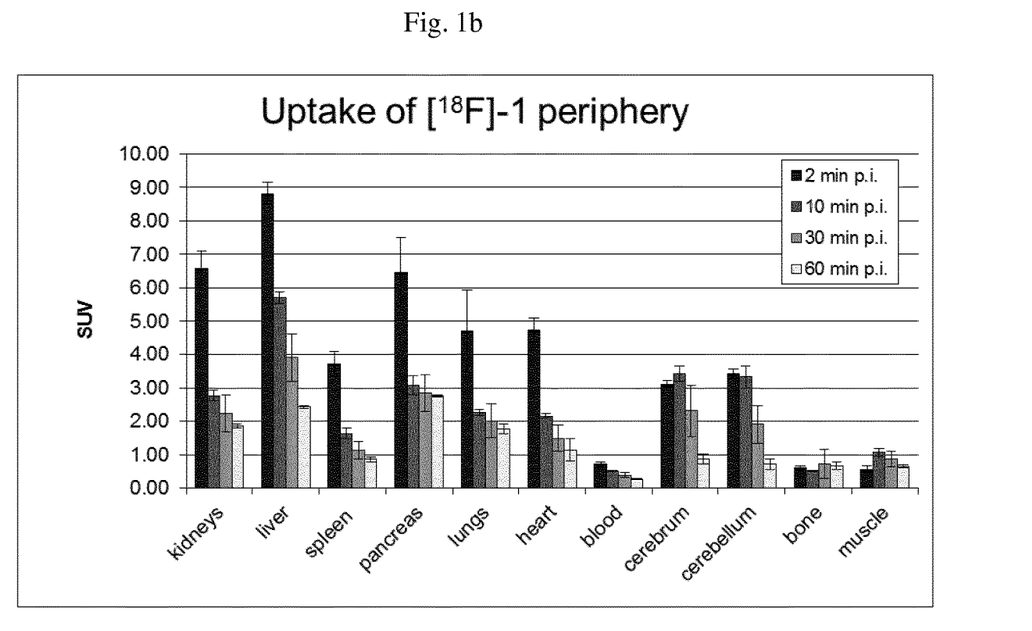
FIG. 1b shows the biodistribution of [$^{18}$F]-1 in the periphery in SD rats.
Figure 2:
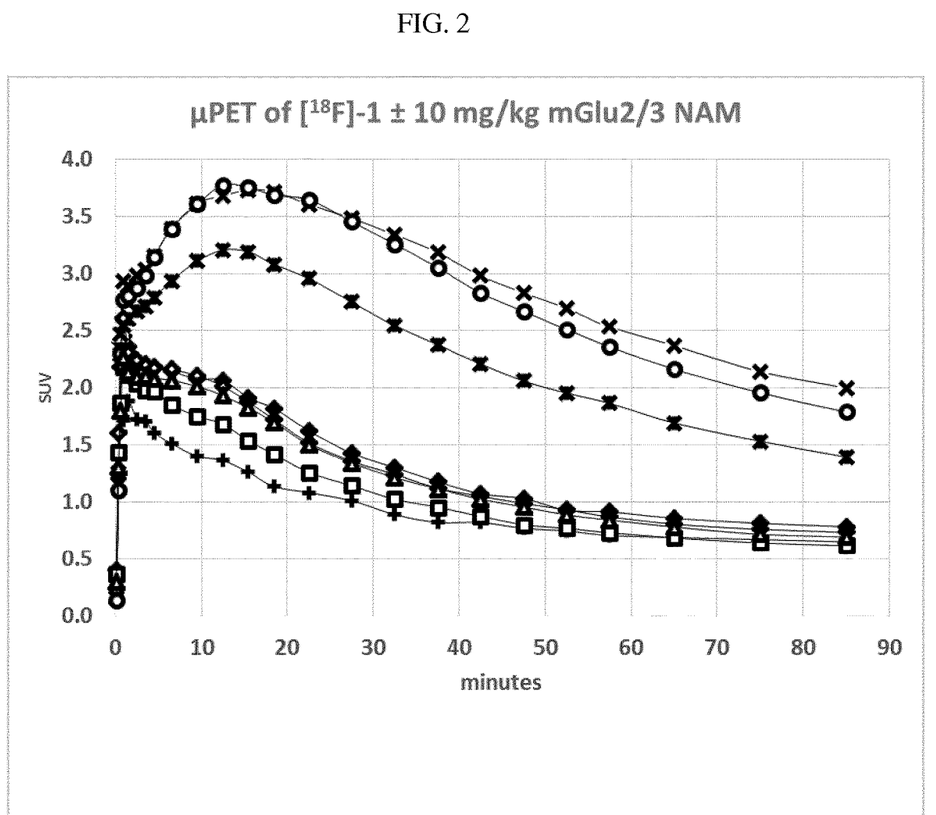

The [$^{18}$F]-1 µPET study showed a high uptake for all brain regions, especially the frontal cortex and the hippocampus, while the pons showed a lower uptake. The peak uptake in frontal cortex during the baseline scan was observed around 15 min after tracer injection. After pretreatment the uptake in the different brain areas was reduced and at the same level as the pons, the uptake in the pons however was also reduced. FIG. 2 shows the time activity curves for the uptake of [$^{18}$F]-1 with and without pretreatment of 10 mg/kg of compound A (a NAM compound, selective for mGlu2/3 (~20 fold selective for 2 over 3) vs other mGluRs) in SD rats.

Discussion

The uptake in the periphery of the ex-vivo biodistribution showed the highest uptake in the liver, as well as a high kidney uptake, followed by urinary excretion. The bone uptake was low at start, but went slightly up over time hinting for some defluorination.

The ex-vivo biodistribution showed a high brain uptake for [$^{18}$F]-1 and a fast washout from the different brain areas. The pons is considered to be a reference region with absence of mGluR2 or mGluR3 expression, while on all other regions both mGluR2 and mGluR3 are present, with the highest expression levels in the cerebral cortex (Farinha A, et al. *BJPharmacol*, 2015, 172, 2383-2396). [$^{18}$F]-1 showed the highest uptake in the cortex, with a low uptake in the pons in combination with a faster washout from the pons compared to the other regions, suggesting a good mGluR2/3 specificity, since the brain uptake reflects the reported distribution pattern for mGluR2/3.

The uptake of [$^{18}$F]-1 was the highest in the frontal cortex and striatum in the PET scan, closely followed by the hippocampus, with peak uptakes of around 15 min after injection. The pons showed a much lower uptake, in the same range as in the other brain regions after pretreatment with compound A, indicating a good mGluR2/3 specificity. Full blocking was observed with time activity curves of frontal cortex and striatum coinciding with that of the pons.

μPET Imaging Studies—Rhesus Monkey

Dynamic 120-min μPET scans with [$^{18}$F]-1 were acquired with a Focus 220 μPET scanner on a rhesus monkey (8 y-old female *Macaca mulatta*, 5.8 kg), that was sedated with ketamine (Ketalar®) and xylazine (Rompun®) via intramuscular (i.m.) injection. During scanning the monkey received repeatedly an additional dose of ketamine/xylazine via i.v. injection. O$_2$ saturation in blood, breathing frequency and heartbeat frequency were monitored during the entire experiment. The head of the animal was placed central in the field of view of the μPET scanner. Scans were acquired in list mode and Fourier rebinned in 27 time frames (4×15 s, 4×60 s, 5×180 s, 8×300 s, 6×600 s). Data were reconstructed using a 3D maximum a posteriori (3D-MAP) iterative reconstruction. TACs of the whole brain were generated using VOIs with PMOD software. Radioactivity concentration in the brain is expressed as SUV as a function of time after tracer injection. In addition, non-displaceable binding potential (BPnd) was determined, using kinetic modeling based on the simplified reference tissue model (SRTM) with the pons as reference region (0-60 min). Scans were started immediately after i.v. injection of 185 MBq of [$^{18}$F]-1 via the vena saphena of the right leg. For the pre-treatment study, the cold authentic reference compound A was dissolved in a vehicle containing 20% (2-hydroxypropyl)-β-cyclodextrin and 2 equivalents HCl, filtered through a 0.22-μm membrane filter (Millex-GV, Millipore) prior to injection. Pre-treatment was done by i.v. injection of 2.5 mg/kg of cold authentic reference compound A, 30 min prior to injection of 185 MBq of [$^{18}$F]-1. μPET images were compared to a baseline scan, acquired in the non-treated monkey. Blood samples were collected during both baseline and pre-treatment scans at 10, 30 and 60 min p.i. via a catheter in the vena saphena of the left leg and plasma was analysed for radio metabolites according to the same procedure as for rats.

Results—μPET Imaging Studies Rhesus Monkey

Figure 3:
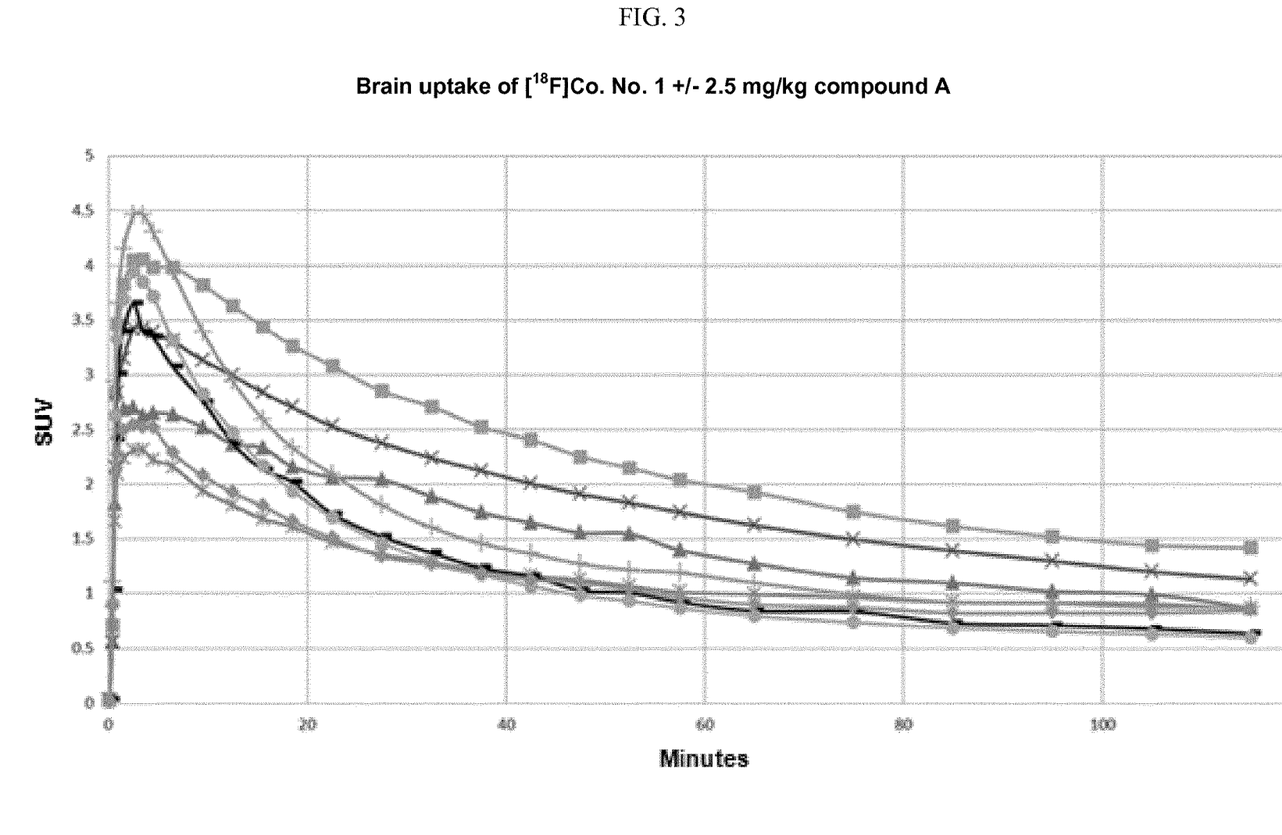
FIG. 3 shows µPET time activity curves for the uptake of [$^{18}$F]-1 with and without pretreatment of 2.5 mg/kg i.v. compound A in a rhesus monkey; a significant blocking effect was observed in all brain regions except in pons.
Figure 4:
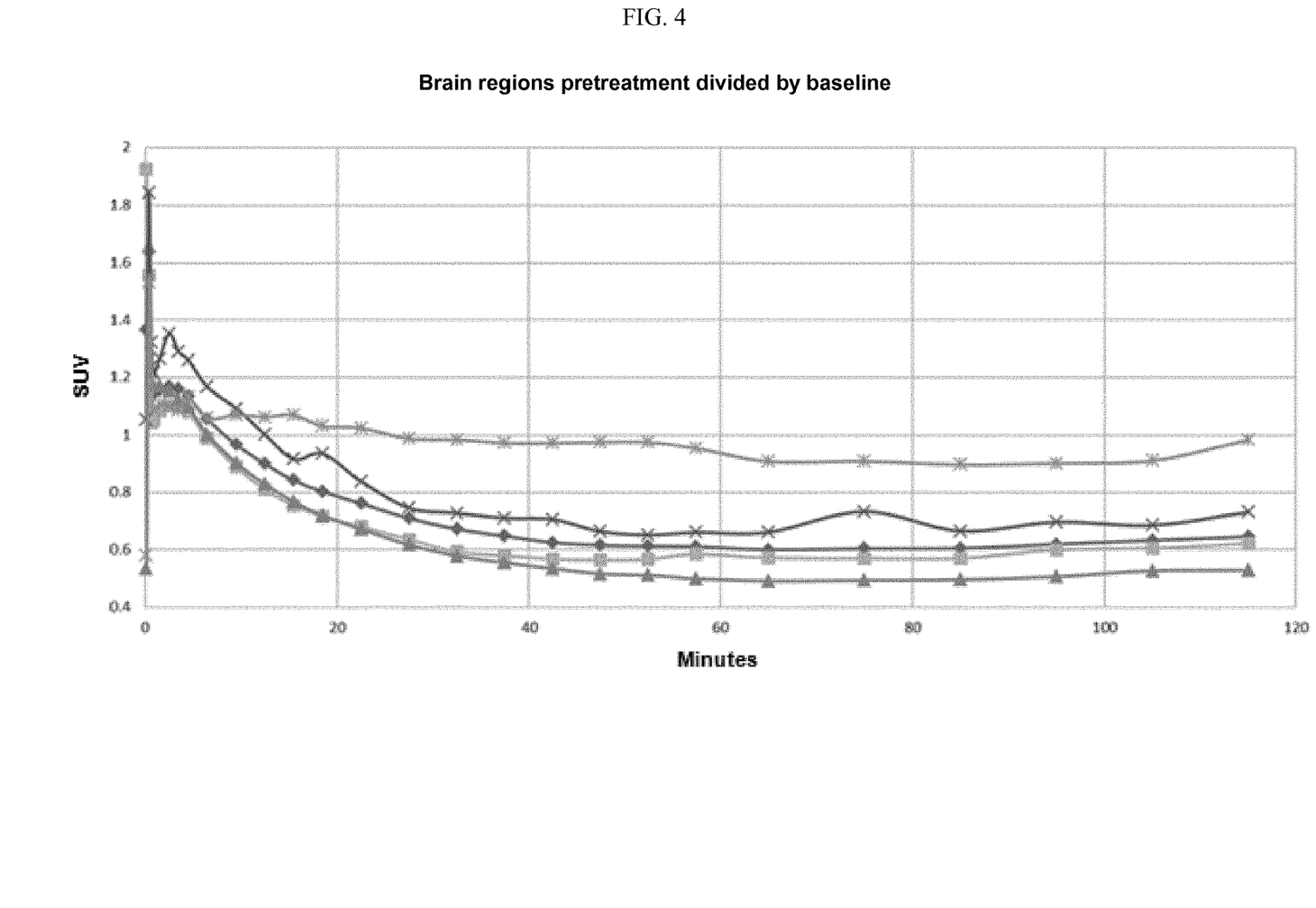
FIG. 4 shows the SUV in brain regions divided by baseline, confirming the blocking effect in all brain regions except pons in a rhesus monkey.
Figure 5:
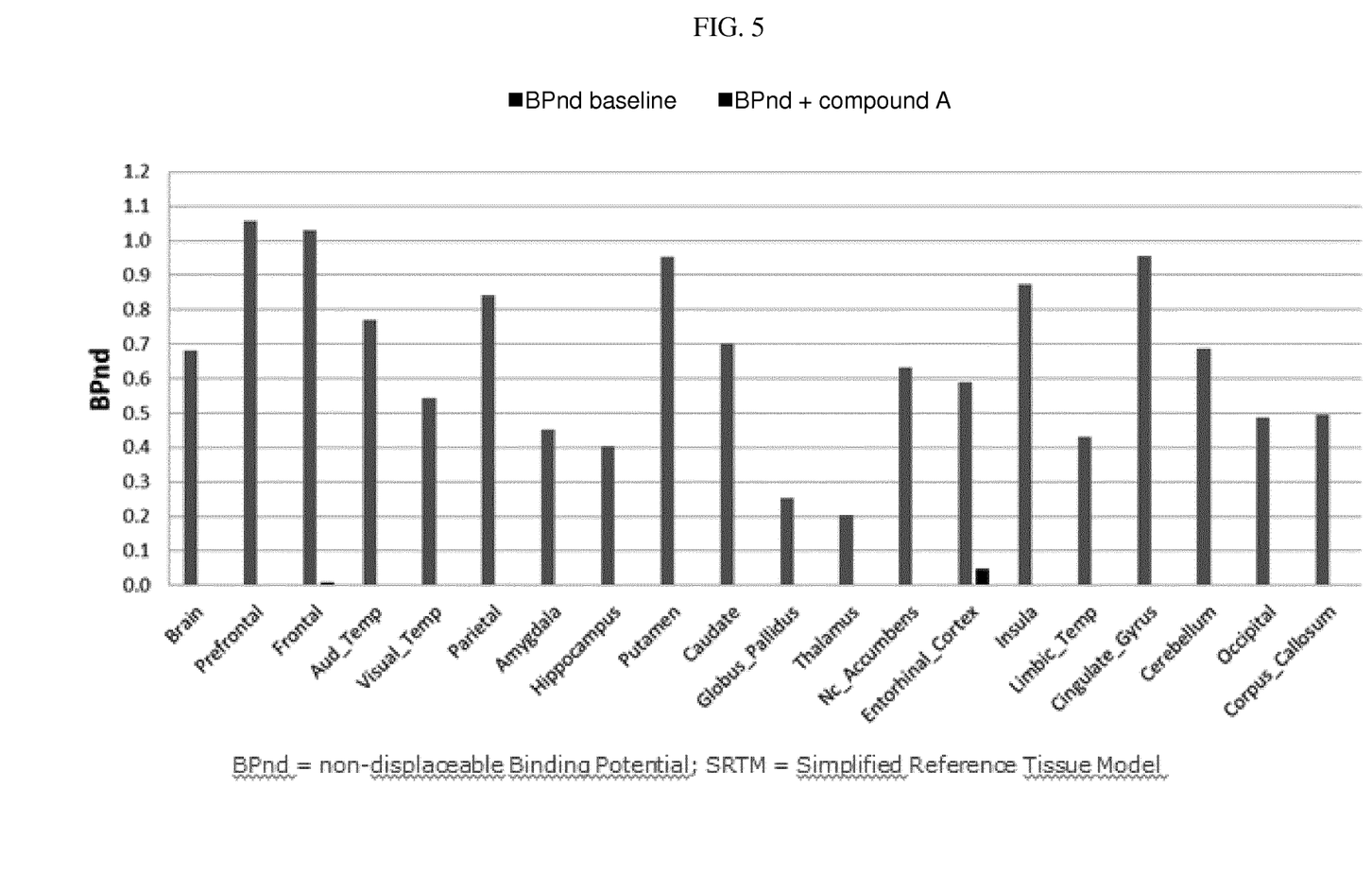
FIG. 5 shows binding potential calculations using Pons as reference in SRTM model over the first 60 minutes in a rhesus monkey; blocking effect in all brain regions using pons as reference was observed.

Results of the 120-min baseline and pre-treatment scan of [$^{18}$F]-1 are shown in FIG. 3. TACs of the baseline scan with [$^{18}$F]-1 show a rapid brain uptake (SUV of ~3 in the whole brain, time to peak uptake: 3.5 min), with high SUVs in the frontal cortex and the cerebellum. Low and comparable SUVs were recorded for the pons in both the baseline and pre-treatment scan, while for the other brain regions the uptake is reduced after pre-treatment with compound A. Ratios of the pre-treatment with the baseline scan of the whole brain, frontal lobe, cerebellum, and hippocampus confirmed this blocking effect (FIG. 4). Furthermore, high BPnd were found both in the frontal and prefrontal cortices, while BPnd was low in the thalamus (FIG. 5). After pre-treatment with 2.5 mg/kg compound A, the BPnd was reduced to zero or near zero in all brain regions. No bone uptake, related to the presence of [$^{18}$F]fluoride or a potential radiometabolite, was seen in any of the μPET scans.

The invention claimed is:

1. A compound having the Formula or a pharmaceutically acceptable salt or a solvate thereof.

2. The compound according to claim 1, having the Formula

3. A compound having the Formula or a pharmaceutically acceptable salt or a solvate thereof.

4. A process for the synthesis of compound comprising
(a) the steps of (a-1) reacting a compound of Formula (P-1) with methanesulfonic anhydride in the presence of a base and an inert solvent, and (a-2) reacting the compound obtained in step (a-1) with [$^{18}$F]F$^-$ in the presence of a base in an inert solvent)

or
(b) the step of reacting a compound of Formula (P-2) with [$^{18}$F]F$^-$ in the presence of a base in an inert solvent or
(c) the step of reacting a compound of Formula (P-3) with [$^{18}$F]F$^-$ in the presence of a base in an inert solvent

* * * * *